(12) United States Patent
Heyrman et al.

(10) Patent No.: US 6,773,424 B2
(45) Date of Patent: Aug. 10, 2004

(54) ABSORBENT ARTICLE HAVING ELASTICIZED SIDE SHIELDS WITH IMPROVED BODY FIT

(75) Inventors: Sheila Marie Heyrman, Appleton, WI (US); David Charles Musil, Appleton, WI (US); Melissa Jean Dennis, Appleton, WI (US); Debra Ann Haase, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 235 days.

(21) Appl. No.: 10/094,040

(22) Filed: Mar. 8, 2002

(65) Prior Publication Data

US 2003/0171732 A1 Sep. 11, 2003

(51) Int. Cl.[7] ................................................. A61F 13/15
(52) U.S. Cl. ................................................. 604/385.24
(58) Field of Search ...................... 604/385.01, 385.04, 604/385.24, 385.25, 385.28

(56) References Cited

U.S. PATENT DOCUMENTS

| | | |
|---|---|---|
| 3,805,790 A | 4/1974 | Kaczmarzyk et al. |
| 3,860,003 A | 1/1975 | Buell |
| 4,681,577 A | 7/1987 | Stern et al. |
| 4,701,177 A | 10/1987 | Ellis et al. |
| 4,770,657 A | 9/1988 | Ellis et al. |
| 4,911,701 A | 3/1990 | Mavinkurve |
| 4,944,735 A | 7/1990 | Mokry |
| 5,032,121 A | 7/1991 | Mokry |
| 5,074,856 A | 12/1991 | Coe et al. |
| 5,181,563 A | 1/1993 | Amaral |
| 5,234,422 A | 8/1993 | Sneller et al. |
| 5,295,988 A | 3/1994 | Muckenfuhs et al. |
| 5,308,346 A | 5/1994 | Sneller et al. |
| 5,387,210 A | 2/1995 | Murakami |
| 5,413,569 A | 5/1995 | Yamamoto |
| 5,447,507 A | 9/1995 | Yamamoto |
| 5,486,168 A | 1/1996 | Runeman et al. |
| 5,542,941 A | 8/1996 | Morita |
| 5,558,659 A | 9/1996 | Sherrod et al. |
| 5,601,544 A | 2/1997 | Glaug et al. |
| 5,613,961 A | 3/1997 | DiPalma et al. |
| 5,618,283 A | 4/1997 | Yamamoto |
| 5,624,426 A | 4/1997 | Roe et al. |

(List continued on next page.)

FOREIGN PATENT DOCUMENTS

| | | |
|---|---|---|
| EP | 0 091 412 B2 | 11/1992 |
| EP | 0 606 082 A1 | 7/1994 |
| EP | 0 680 739 A1 | 8/1995 |
| EP | 0 556 996 B1 | 7/1997 |
| EP | 0 600 494 B1 | 4/1999 |
| GB | 2 296 445 A | 7/1996 |

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

INDA Standard Test Method IST 70.4 (01), "Standard Test Method for Water Vapor Transmission Rates of 500 to 100,000 gm/m$^2$ Day Through Nonwoven Fabrics and Plastic Barriers," Copyright 2001, pp. 129–133.

*Primary Examiner*—John J. Calvert
*Assistant Examiner*—Michael Bogart
(74) *Attorney, Agent, or Firm*—Ralph H. Dean, Jr.

(57) ABSTRACT

An absorbent article having a narrow crotch portion and elasticized shield shields is disclosed. The absorbent article has a fit factor defined as the minimum crotch width divided by the effective height of the side shields. In one embodiment, the absorbent article includes and an absorbent structure having a central portion defined by a width about 65 millimeters or less, and a length about 50 millimeters or greater, and the absorbent article having a fit factor less than about 7.0.

22 Claims, 2 Drawing Sheets

U.S. PATENT DOCUMENTS

| | | |
|---|---|---|
| 5,704,928 A | 1/1998 | Morita et al. |
| 5,752,945 A | 5/1998 | Mosley et al. |
| 5,752,946 A | 5/1998 | Boberg et al. |
| 5,810,800 A | 9/1998 | Hunter et al. |
| 5,820,618 A | 10/1998 | Roberts et al. |
| 5,851,204 A | 12/1998 | Mizutani |
| 5,921,975 A | 7/1999 | Suzuki et al. |
| 6,126,648 A | 10/2000 | Keck et al. |
| 6,159,190 A | 12/2000 | Tanaka et al. |
| 6,171,290 B1 | 1/2001 | Boisse et al. |
| 6,231,554 B1 | 5/2001 | Menard |
| 6,315,765 B1 | 11/2001 | Datta et al. |
| 6,315,766 B1 | 11/2001 | Drevik |
| 6,613,955 B1 * | 9/2003 | Lindsay et al. ............. 604/378 |

* cited by examiner

ABSORBENT ARTICLE HAVING ELASTICIZED SIDE SHIELDS WITH IMPROVED BODY FIT

BACKGROUND OF THE INVENTION

The comfort of an absorbent article, such as an incontinence pad, during use is a primary factor in the design of the pad. A frequent problem with pads is that they bunch and twist during use, especially during periods of activity by the wearer. Variously shaped pads, increasingly thinner pads, and more flexible pads have been developed in order to improve the comfort during use.

In addition to providing a comfortable pad, it is especially important for the pad to fully contain all body exudates to prevent leakage and the soiling of clothes and the body. While shaped and thinner pads have increased user comfort, these pads frequently have less leakage protection when compared to thicker and wider pads. The reason for this is there simply is less material present in the crotch region to prevent leaks. As the pad becomes thinner and/or narrower there is more chance for leakage especially if the pad moves, bunches, or twists while in use. The chance for leakage is especially pronounced in incontinent pads resulting from urine's lower viscosity and the larger amount present for containment as compared to menses in a sanitary napkin.

To address leakage, some pads are designed with upstanding side shields adjacent the absorbent structure to prevent lateral leakage. However, the shields are frequently not effective to prevent all lateral leakage. The ineffectiveness results from shields that fail to stand up as intended after folding and packaging, shields that are too short to be effective, or shields that fail to eliminate all possible channels or pathways for leakage.

Therefore what is needed is an absorbent article that is comfortable to wear, prevents bunching and twisting during use, and is effective against side leakage especially for urine.

SUMMARY OF THE INVENTION

It has now been found that an improved pad that is comfortable to wear results when the central portion of the absorbent layer has a width about 65 millimeters or less and a length about 50 millimeters or greater, and the pad has a fit factor less than about 7.0. The fit factor is the ratio of the minimum crotch width to the effective shield height. The fit factor takes into account user comfort by the minimum crotch width variable and side leakage protection by the effective shield height variable. As the ratio becomes larger, the pad will be less comfortable having a wider width at the narrowest point of the crotch and more prone to leakage from a smaller effective shield height. As the ratio gets smaller the pad becomes more comfortable to wear, has reduced bunching and twisting, and has enhanced leakage protection.

In one aspect, the invention resides in an absorbent article having a longitudinal axis, a transverse axis, a first side, and a second side including: a topsheet; a bottomsheet; an absorbent structure positioned between the topsheet and the bottomsheet, the absorbent structure having a central portion defined by a width about 65 millimeters or less, and a length about 50 millimeters or greater; a pair of side shields formed on opposite sides of the absorbent structure by a first elastic member adjacent the first side and a second elastic member adjacent the second side, the first and second elastic members contracting at least a portion of the first and second sides, each of the side shields having an upstanding end and a terminal end adjacent the absorbent structure, the side shield having an effective height defined as the maximum vertical distance from the terminal end to the upstanding end; and the absorbent article having a minimum crotch width defined as the minimum transverse dimension between the terminal ends, the absorbent article having a fit factor defined as the minimum crotch width divided by the effective height, and the fit factor is less than about 7.0.

In another aspect, the invention resides in an absorbent article having a longitudinal axis, a transverse axis, a first side and a second side including: a topsheet; a bottomsheet; an absorbent structure positioned between the topsheet and the bottomsheet, the absorbent structure generally hour glass in shape having a first lobe, a central portion, and a second lobe, the central portion defined by a width about 65 millimeters or less, and a length greater about 50 millimeters or greater; a pair of side shields formed on opposite sides of the absorbent structure by a first elastic member adjacent the first side and a second elastic member adjacent the second side, the first and second elastic members contracting at least a portion of the first and second sides, each of the side shields having an upstanding end and a terminal end adjacent the absorbent structure, the side shield having an effective height defined as the maximum vertical distance from the terminal end to the upstanding end; and the absorbent article having a crotch width defined as the minimum transverse dimension between the terminal ends, the absorbent article having a fit factor defined as the crotch width divided by the effective height, and the fit factor is less than about 7.0.

In an additional aspect, the invention resides in an absorbent article having a longitudinal axis, a transverse axis, a first side, and a second side including: a topsheet; a bottom sheet; an absorbent structure having a first layer and a second layer positioned between the topsheet and the bottomsheet, the first layer adjacent the bottomsheet and generally hour glass in shape having a first lobe, a central portion, a second lobe, and a periphery, the central portion defined by a width about 65 millimeters or less, and a length about 50 millimeters or greater; the second layer adjacent the first layer and having a perimeter; the periphery of the first layer extending past the perimeter of the second layer; a transfer layer adjacent the second layer; a pair of side shields formed on opposite sides of the absorbent structure by a first elastic member adjacent the first side and a second elastic member adjacent the second side, the first and second elastic members contracting at least a portion of the first and second sides, each of the side shields having an upstanding end and a terminal end adjacent the absorbent structure, the side shield having an effective height defined as the maximum vertical distance from the terminal end to the upstanding end; and the absorbent article having a crotch width defined as the minimum transverse dimension between the terminal ends, the absorbent article having a fit factor defined as the crotch width divided by the effective height, and the fit factor is less than about 7.0.

BRIEF DESCRIPTION OF THE DRAWINGS

The foregoing aspects of the invention, and other features, aspects, and advantages of the invention will become better understood with regard to the following description, appended claims, and accompanying drawings where:

DEFINITIONS

As used herein "liquid impermeable" means a material, as tested by a hydrohead, which is capable of supporting at least about 20 cm of water without substantial leakage therethrough. A suitable technique for determining the resistance of a material to liquid penetration is Federal Test Methods Standard N. 191A Method 5514—"Water Resistance of Cloth; Low Range: dated Jul. 20, 1978.

As used herein "joined" includes configurations where one element is directly or indirectly attached to another element by an means including, but not limited to, adhesives, thermal bonding, sonic bonding, chemical bonding, mechanical bonding, pressure bonding, heat and pressure bonding, hydrogen bonding, fasteners, stitching or other means know to those of skill in the art. Joined also includes elements indirectly joined together. By "indirectly joined" it is meant one element is attached to a second element by one or more intermediate layers. For instance, the outer layers in an ordinary plywood laminate are indirectly joined to each other by the laminate's other layers.

As used herein "vapor permeable" means a material that permits the transmission of water vapor and other gases. Vapor permeable or "breathable" materials will have a water vapor transmission rate (WVTR) of about 300 grams or greater of $H_2O/m^2/24$ hours. A suitable test method for testing the vapor permeability of materials is INDA standard test IST 70.4(01) "Standard Test Method for Water Vapor Transmission Rates of 500 To 100,000 $gm/m^2$ day Through Nonwoven Fabrics and Plastic Barriers." The Association of the Nonwovens Fabric Industry in Cary, N.C. publishes the test method.

DETAILED DESCRIPTION OF THE INVENTION

Figure 1:
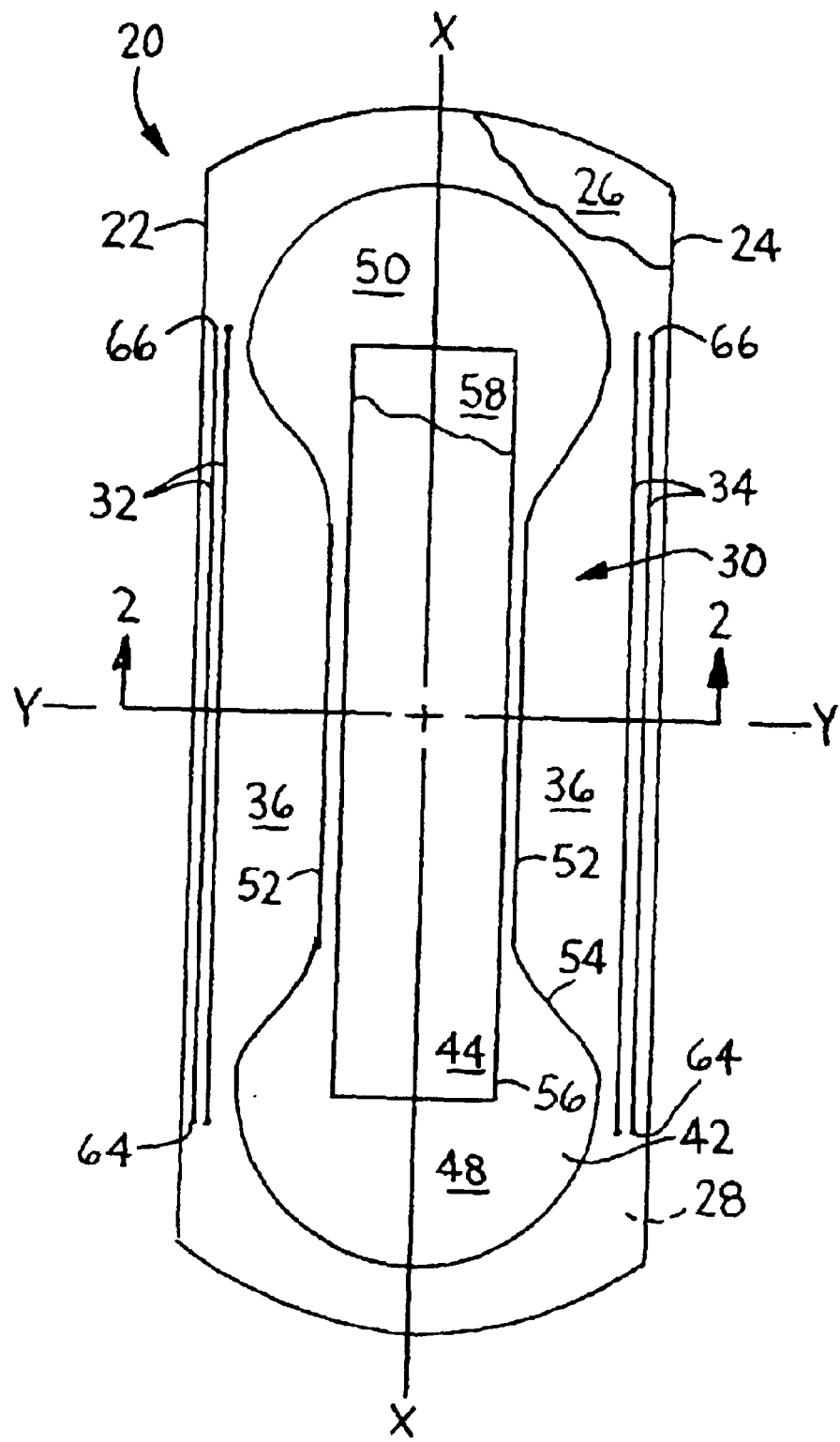
FIG. 1 is a plan view of one embodiment of the absorbent article.
Figure 2:
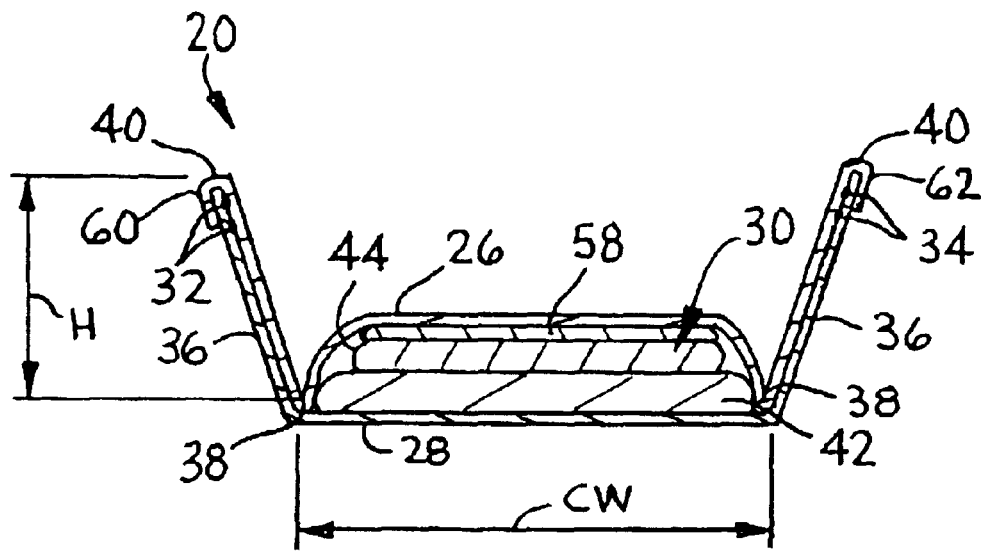
FIG. 2 is a cross-section view of FIG. 1 taken along line 2—2.

Referring to FIGS. 1 and 2, an embodiment of the absorbent article 20 is shown in plan view. In FIG. 1 portions of the drawings are cut away to reveal the underlying structure. The absorbent article has a longitudinal axis X—X, a transverse axis Y—Y, a first side 22, and a second side 24. The absorbent article 20 includes a topsheet 26, a bottomsheet 28, and absorbent structure 30 disposed between the topsheet 26 and the bottomsheet 28. Adjacent the first side 22 is a first elastic member 32 and adjacent the second side 24 is a second elastic member 34. The first and second elastic members, 32 and 34, contract at least a portion of the first and second sides, 22 and 24, forming a pair of side shields 36.

The side shields 36 can be an integral portion of the topsheet, or the bottomsheet, or formed from the topsheet and the bottomsheet, or the side shields can be a separate member joined to the absorbent article. The side shields 36 each have a terminal end 38 adjacent the absorbent structure 30, and an upstanding end 40 formed by the first and second elastic members, 32 and 34 contracting the first and second sides, 22 and 24. The side shields 36 have an effective height H as measured by placing a ruler adjacent the terminal end 38 inside of the absorbent article and measuring vertically to the upstanding end 40 while the pad is resting on a horizontal surface. See FIG. 2 illustrating the dimension H. If the side shields differ in height from one side of the absorbent article to the other, the effective height H is the larger of the two dimensions. It is important to measure this dimension vertically because frequently the side shields of absorbent articles, especially after folding and packaging, often fail to fully standup and instead the side shields bunch and contract the sides of the absorbent article. In such a case, the upstanding end 40 can be actually lower than the top of the absorbent structure 30. Thus, even though the side shield 36 may appear to have a sufficient size when observed in a plan view, it is the vertical height that prevents lateral leakage in use, and thus the necessity to determine the vertical effective height H.

The terminal ends 38 of the side shields 36 also determine another important dimension for the fit of the absorbent article. That dimension is a minimum crotch width CW, which is the minimum lateral distance between the terminal ends 38. The minimum crotch width is measured at the narrowest location between the terminal ends 38. Often this is easiest to perform by measuring transversely across the bottom of the absorbent article. However, depending of the exact location of the terminals ends 38, it may be necessary to measure this dimension inside of the absorbent article. Desirably the crotch width CW is about 65 millimeters or less for user comfort. More desirable the crotch width CW about 55 millimeters or less, and more desirable still the crotch width CW is about 45 millimeters or less.

Once the effective shield height H and minimum crotch width CW are measured, a fit factor for the absorbent article can be determined. The fit factor is the ratio of the minimum crotch width to the effective shield height.

$$\text{Fit Factor} = CW/H$$

The fit factor takes into account user comfort by the minimum crotch width variable and side leakage protection by the effective shield height variable. As the ratio becomes larger the pad will be less comfortable having a wider width at the narrowest point of the crotch, and more prone to leakage from a smaller effective shield height. As the ratio gets smaller the pad becomes more comfortable to wear, has reduced bunching and twisting, and has enhanced leakage protection. The fit factor ratio captures both comfort and leakage protection in a single number with a lower ratio preferred. Desirably, the fit factor of the absorbent article is about 7.0 or less. More desirable the fit factor is about 5.0 or less, and more desirable yet the fit factor is about 3.0 or less.

Figure 3:
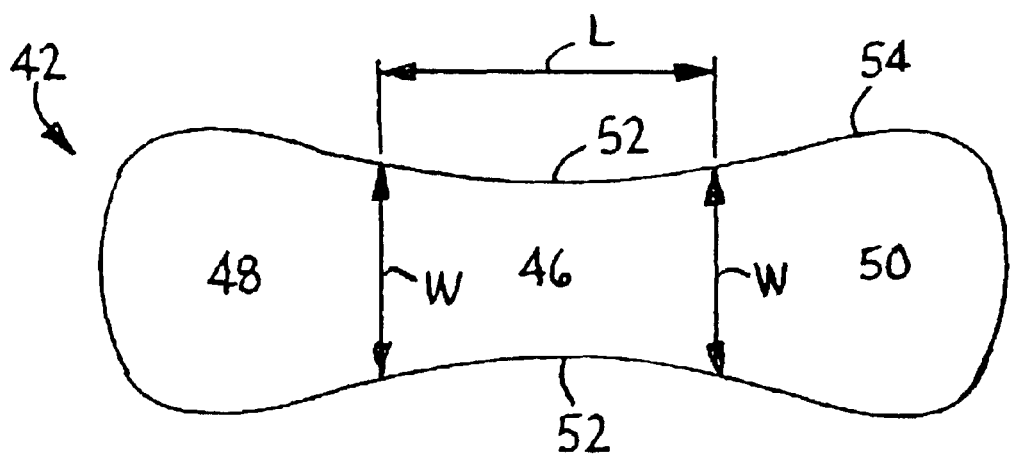
FIG. 3 is a plan view illustrating the dimensions for the central portion of the absorbent structure.

Referring now to FIGS. 2 and 3, the absorbent article's absorbent structure 30 has a primary absorbent layer 42 and can also include a secondary absorbent layer 44 if desired. The primary absorbent layer 42 has a central portion 46, and can be hour glass or dog bone in shape having a first lobe 48 and a second lobe 50. In order for the absorbent article to fit comfortably, it has been determined that the central portion 46 must have a width W about 65 millimeters or less and that the length L of the central portion where the width W is 65 millimeters or less must be about 50 millimeters or greater. More desirable the length L of the central portion is about 70 millimeters or greater, and more desirable yet the length L of the central portion is about 90 millimeters or greater.

These dimensions are needed to insure that the primary absorbent layer 42 has a width W that is comfortable and that the length L is sufficient to extend throughout the crotch region for comfort. It is also important that the length L is long enough to ensure that absorbent article will cup from the contraction of the first and second elastic members, 32 and 34, and reduced stiffness of the primary absorbent layer in the central portion 46. In addition, it is possible to design an absorbent article with a low fit factor by having a narrow crotch width CW in only a very short length of the central portion, but then if the pad quickly widens out the absorbent article can still be uncomfortable to wear. In other words, the portion of the pad where the fit factor is low must be sufficiently long to ensure a comfortable fitting absorbent article.

The central portion 46 has a pair of side edges 52 that can be linear as shown in FIG. 1 or that can be curvilinear as shown in FIG. 3. Desirably the side edges 52 are linear because it has been determined that a linear side edge 52 for the central portion 46 not only enhances comfort, but also increases the effective height H of the side shields 36. This reduces the fit factor of the absorbent article resulting in increased comfort and reduced leakage for the absorbent article. The linear side edges 52 increase the effective height H because the first and second elastic members, 32 and 34, will form a deep trough in the central portion 46 as they contract the side edges, 22 and 24, as illustrated in FIG. 2. When the side edges 52 are curvilinear as illustrated in FIG. 3, the first and second elastic members, 32 and 34, are pulled more out of the vertical plane in the central portion 46 and the resulting side shields 36 have a reduced effective height H.

The topsheet 26 is liquid permeable such that body exudates can pass through the liner and be absorbed by the absorbent structure. The topsheet has a first edge 60 and a second edge 62. In one embodiment, the first and second edges, 60 and 62, are folded over the upstanding ends 40 and joined to the bottomsheet along the first and second sides, 22 and 24, as shown in FIG. 2. The folded edges, 60 and 62, of the topsheet ensure the first and second elastic members, 32 and 34, are securely attached to the first and second edges by the adhesive used to place and join the elastic members, the topsheet, and the bottomsheet together. The folded edges, 60 and 62, also provide a soft comfortable surface to the upstanding ends 40 for contact with the body. In addition, the folded edges, 60 and 62, improve the durability of the upstanding ends 40 by preventing adhesive delamination of the topsheet and bottomsheet along the first and second sides. Finally, the folded edges, 60 and 62, also slightly stiffen the upstanding ends 40, which promotes more uniform gathers after the first and second sides, 22 and 24, are contracted resulting in a better appearing, more uniform, absorbent article.

Suitable topsheet 26 materials can include a nonwoven web, a spunbond, a meltblown, or a bonded carded web composed of synthetic polymer fibers, such as polypropylene, polyethylene, polyesters or the like, an apertured film, or a web of natural fibers such as rayon or cotton. In one embodiment, the topsheet was a 17.0 gsm sheath/core bicomponent polypropylene and polyethylene filament spundbond. The spunbond was treated with a wetting agent in the amount of 0.55% by weight of Ahcovel. The spunbond is commercially available from Kimberly-Clark Corporation having offices in Neenah, Wis.

The bottomsheet 28 can be liquid permeable or liquid impermeable, and vapor permeable or vapor impermeable. For example, the absorbent article can be used as an insert and placed into an adult incontinence brief. In such a case, the bottom layer would be liquid permeable, and the side flaps 36 can be liquid impermeable. The combination of the absorbent article and brief would have enhanced lateral leakage protection, delay urine migration into the brief, and have increased the capacity.

The bottomsheet 28 can be a single layer or a laminate of one or more layers such as a film layer laminated to a nonwoven layer. Suitable bottomsheet materials can include films, wovens, and nonwovens. In one embodiment, the bottomsheet was a vapor permeable 35.6 gsm highly breathable stretched thermal laminate (HBSTL) having a WVTR of about 6,400 gm $H_2O/m^2/24$ hours or greater. HBSTL is a laminate of an apertured polyethylene film layer to a polypropylene nonwoven layer, and HBSTL is commercially available from Kimberly-Clark Corporation having offices in Neenah, Wis.

Ordinarily the bottomsheet 28 will have areas of pressure sensitive garment adhesive applied for securing the absorbent article to undergarments or other absorbent articles while in use. Typically, the garment adhesive is covered by a release paper to prevent contamination until just before applying the absorbent article to the undergarment. Suitable adhesives and release papers are known to those of ordinary skill in the art.

The absorbent structure 30 can be a single layer or a multilayer structure of materials that absorb bodily exudates such as fibers of cellulose, rayon, or cotton, polymer foams, and superabsorbents such as a partially neutralized polyacrylic acid. The individual layers can contain only fibers, such as cellulose, only superabsorbents, or layers containing both fibers and superabsorbents in a homogeneous mixture. Desirably, the absorbent article has a saturated retention capacity of about 75 grams or greater as tested by the Saturation Retention Capacity test in the Test Methods Section. More desirable the absorbent article has a saturated retention capacity of between about 100 grams to about 500 grams.

In one embodiment, the absorbent structure 30 included the primary absorbent layer 42 having a periphery 54 and the secondary absorbent layer 44 having a perimeter 56. The periphery 54 extends past the perimeter 56 on all sides of the secondary absorbent layer 44 as shown in FIG. 1. Such a design for the absorbent structure provides enhanced leakage protection. In this embodiment, both the primary and secondary absorbent layers are a homogeneous mixture of a Weyerhaeuser CF416 fluff pulp and a Dow Chemical DRYTECH® 2035M superabsorbent. The fluff is commercially available from Weyerhaeuser Company having an office in Federal Way, Wash., and the superabsorbent is commercially available from Dow Chemical Company having an office in Midland, Mich. The primary absorbent layer contained 4.7 grams of fluff and 43.5% superabsorbent by weight. The secondary absorbent layer contained 10.6 grams of fluff and 11.8% superabsorbent by weight.

A transfer layer 58 can be placed between the secondary absorbent layer 44 and the topsheet 26 if desired. The transfer layer 58 functions to quickly uptake body exudates and discharge them into the absorbent structure 30. Suitable transfer materials include any woven or nonwoven web adapted to quickly take in and/or transport liquids. For example, the transfer layer 58 can include a nonwoven layer of a spunbonded, a meltblown, or a bonded-carded web composed of synthetic polymer filaments or fibers, such as polypropylene, polyethylene, polyesters or the like, or a web of natural polymer filaments or fibers such as rayon or cotton. In one embodiment, the transfer layer was 50.8 gsm side-by-side bicomponent polypropylene/polyethylene filament spunbond PRISM material treated with 2.25% by weight Ahcovel and SF-19 (2:1 ratio) wetting agent. PRISM is commercially available from Kimberly-Clark Corporation having offices in Neenah, Wis.

The first and second elastic members, 32 and 34, can include any natural rubber, synthetic elastic material, or heat shrinkable material. Each of the first and second elastic members can be a single elastic element or two or more elastic elements operatively associated together. The first and second elastic members are operatively joined to the first and second sides, 22 and 24, by any convenient method such as adhesives. In one embodiment, each of the first and second elastic members included two strands of a dry-spun coalesced multifilament elastomeric thread sold under the tradename LYCRA® and available from E. I. Du Pont de Nemours and Company. Suitable elastomeric threads range from about 500 to about 1,300 decitex (0.05 g/m to 0.13 g/m), and desirable percent elongations of the unstretched length to the stretched length, after application to the absorbent article, are about 250% to about 300% percent.

The first and second elastic members, 32 and 34, each have a first end 64 and a second end 66. In order to maximize leakage protection, the first and second ends, 64 and 66, can terminate adjacent the primary absorbent layer 42, and desirably terminate adjacent the primary absorbent layer where the transverse width of the first and second lobes, 48 and 50, are greatest as shown in FIG. 1. If the first and second ends, 64 and 66, terminate a significant distance away from the primary absorbent layer 42 there is a potential for a channel or pathway to form between the side shields 36 and the primary absorbent layer 42. Such a channel or pathway can allow body exudates to leak and escape between the primary absorbent layer 42 and the side shields 36 past the first and second sides, 22 and 24, of the absorbent article.

Desirably, the first and second elastic members have a length from the first end 64 to the second end 66 in the longitudinal direction greater than or equal to the length of the central portion 46 of the absorbent structure. More desirable, the length of the elastic members from the first end 64 to the second end 66 is about 75 millimeters or greater. More desirable yet, the length of the elastic members from the first end 64 to the second end 66 is about 100 millimeters or greater.

The first and second elastic members desirably are located in close proximity to the first and second sides, 22 and 24. This not only maximizes the effective height H of the side shields 36, but also serves to best cup and shape the entire absorbent article. In addition, having the first and second ends, 64 and 66, terminate adjacent the primary absorbent layer where the transverse width of the first and second lobes, 48 and 50, are greatest also increases the cupping of the pad and the effective height H of the side shields 36. The increased cupping results from the elastic members contracting the first and second sides, 22 and 24, between the first and second lobes, 48 and 50; the reduced stiffness of the central portion 46; and the increased stiffness of the first and second lobes, 48 and 50, preventing the elastic members from contracting the first and second lobes in a transverse direction.

It is possible to locate the first and second elastic members on either side of the bottomsheet 28, right at the first and second sides, 22 and 24, or to wrap the elastic members around the first and second sides. The first and second elastic members 32, and 34, desirably are located about 10 millimeters or less from the first and second side edges, 22 and 24. More desirable, the first and second elastic members 32, and 34, are located about 7 millimeters or less from the first and second side edges, 22 and 24. Still more desirable, the first and second elastic members 32, and 34, are located about 5 millimeters or less from the first and second side edges, 22 and 24.

TEST METHODS

Saturated Retention Capacity

The saturated retention capacity of an absorbent article (pad) or material is measured as follows. The pad to be tested, having a moisture content of less than about 7 weight percent, is weighed and then submerged in an excess quantity of room temperature (about 23 degrees Celsius) 0.9% saline solution. The 0.9% aqueous soluble isotonic saline is commercially available from Ricca Chemical Company having an office in Arlington, Tex. The pad to be tested is allowed to remain submerged for 20 minutes. After 20 minutes, the pad is removed from the saline and placed on a TEFLON® coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The pad is weighed. The amount of fluid retained by the pad being tested is determined by subtracting the dry weight of the pad from the wet weight of the pad (after application of the vacuum) and is reported as the saturated retention capacity in grams of fluid retained.

If material, such as superabsorbent material or fiber from the pad is drawn through the fiberglass screen while on the vacuum box, a screen having smaller openings should be used. Alternatively, a piece of tea bag material can be placed between the pad and the screen and the final value adjusted for the fluid retained by the tea bag material. Suitable tea bag material is a heat sealable tea bag material grade 542, commercially available from Kimberly-Clark Corporation. The amount of fluid absorbed by the tea bag material is determined by performing the saturated retention capacity test on an empty tea bag. Testing of superabsorbent materials or fibers alone can be accomplished using a sealed pouch of tea bag material.

EXAMPLES

The invention was compared to prior commercially available adult incontinent pads intended for moderate to high insult levels. Each of the pads had a saturated retention capacity in excess of 250 grams and was identified as an Ultra absorbency pad. For the POISE® pads, the number identifies the year the product was commercially produced by Kimberly-Clark Corporation and sold. The SERENITY® and ASSURANCE® pads (manufactured by SCA Corporation and Tyco Corporation respectively) were purchased in the Appleton, Wis. area in 2002. Example 1 was a machine produced limited production run within the scope of the invention for experimental testing. Example 2 was a handmade sample within the scope of the invention for experimental testing.

TABLE 1

COMPARATIVE DATA

| Pad Identification | Crotch Width CW (mm) | Effective Height H (mm) | Fit Factor | Length Central Portion L (mm) |
| --- | --- | --- | --- | --- |
| 1999 POISE ® | 72.0 | 15.0 | 4.8 | NA |
| 2001 POISE ® | 71.6 | 6.2 | 11.6 | 60 |
| 2002 POISE ® | 70.4 | 7.7 | 9.1 | NA |
| SERENITY ® | 74.2 | 8.4 | 8.8 | NA |
| ASSURANCE ® | 79.8 | 15.0 | 5.3 | NA |
| Example 1 | 57.2 | 11.7 | 4.9 | 115 |
| Example 2 | 55.0 | 23.0 | 2.4 | 115 |

The data in Table 1 was obtained by measuring the effective shield height H and minimum crotch width CW to the nearest millimeter for five samples and averaging the result. As seen in Table 1, most of the comparative products do not have a central portion with a width about 65 millimeters or less (thus the not applicable result NA), and that the invention has a length for the central portion significantly greater than the other products. In addition, the fit factor of the invention is low indicating a comfortable fitting article with good leakage protection.

It will be appreciated that the foregoing background, summary, and detailed description of the invention are given for the purposes of illustration, and as such are not intended to be construed as limiting the scope of the invention, which is defined by the following claims and all equivalents thereto.

We claim:

1. An absorbent article having a longitudinal axis, a transverse axis, a first side, and a second side comprising:
   a topsheet;
   a bottomsheet;
   an absorbent structure positioned between the topsheet and the bottomsheet, the absorbent structure having a central portion defined by a width about 65 millimeters or less, and a length about 50 millimeters or greater;
   a pair of side shields formed on opposite sides of the absorbent structure by a first elastic member adjacent the first side and a second elastic member adjacent the second side, the first and second elastic members contracting at least a portion of the first and second sides, each of the side shields having an upstanding end and a terminal end adjacent the absorbent structure, the side shield having an effective height defined as the maximum vertical distance from the terminal end to the upstanding end; and
   the absorbent article having a minimum crotch width defined as the minimum transverse dimension between the terminal ends, the absorbent article having a fit factor defined as the minimum crotch width divided by the effective height, and the fit factor is about 7.0 or less.

2. The absorbent article of claim 1 wherein the fit factor is about 5.0 or less.

3. The absorbent article of claim 1 wherein the fit factor is about 3.0 or less.

4. The absorbent article of claim 1 wherein the length of the central portion is about 70 millimeters or greater.

5. The absorbent article of claim 1 where the length of the central portion is about 90 millimeters or greater.

6. The absorbent article of claim 1 wherein the bottomsheet is liquid permeable and the side shields are liquid impermeable.

7. The absorbent article of claim 1 wherein the bottomsheet and side shields are liquid impermeable and vapor permeable.

8. The absorbent member of claim 1 wherein the first and second elastic members are disposed about 10 millimeters or less from the first and second sides.

9. The absorbent article of claim 1 wherein the absorbent article has a saturated retention capacity about 75 grams or greater.

10. An absorbent article having a longitudinal axis, a transverse axis, a first side and a second side comprising:
    a topsheet;
    a bottomsheet;
    an absorbent structure positioned between the topsheet and the bottomsheet, the absorbent structure generally hour glass in shape having a first lobe, a central portion, and a second lobe, the central portion defined by a width about 65 millimeters or less, and a length about 50 millimeters or greater;
    a pair of side shields formed on opposite sides of the absorbent structure by a first elastic member adjacent the first side and a second elastic member adjacent the second side, the first and second elastic members contracting at least a portion of the first and second sides, each of the side shields having an upstanding end and a terminal end adjacent the absorbent structure, the side shield having an effective height defined as the maximum vertical distance from the terminal end to the upstanding end; and
    the absorbent article having a crotch width defined as the minimum transverse dimension between the terminal ends, the absorbent article having a fit factor defined as the crotch width divided by the effective height, and the fit factor is less than about 7.0.

11. The absorbent article of claim 10 wherein the central portion includes a pair of side edges and the side edges are linear.

12. The absorbent article of claim 10 wherein the minimum crotch width is about 55 millimeters or less.

13. The absorbent article of claim 10 wherein the absorbent article has a saturated retention capacity of about 75 grams or greater.

14. The absorbent article of claim 10 wherein each of the first and second elastic members have a first end and a second end, the first end adjacent the first lobe and the second end adjacent the second lobe.

15. The absorbent article of claim 14 wherein the first ends terminate where the first lobe has a maximum transverse width, and the second ends terminate where the second lobe has a maximum transverse width.

16. An absorbent article having a longitudinal axis, a transverse axis, a first side, and a second side comprising:
    a topsheet;
    a bottom sheet;
    an absorbent structure having a first layer and a second layer positioned between the topsheet and the bottomsheet, the first layer adjacent the bottomsheet and generally hour glass in shape having a first lobe, a central portion, a second lobe, and a periphery, the central portion defined by a width about 65 millimeters or less, and a length about 50 millimeters or greater; the second layer adjacent the first layer and having a perimeter; and the periphery of the first layer extending past the perimeter of the second layer;
    a transfer layer adjacent the second layer;
    a pair of side shields formed on opposite sides of the absorbent structure by a first elastic member adjacent the first side and a second elastic member adjacent the second side, the first and second elastic members contracting at least a portion of the first and second sides, each of the side shields having an upstanding end and a terminal end adjacent the absorbent structure, the side shield having an effective height defined as the maximum vertical distance from the terminal end to the upstanding end; and
    the absorbent article having a crotch width defined as the minimum transverse dimension between the terminal ends, the absorbent article having a fit factor defined as the crotch width divided by the effective height, and the fit factor is about 7.0 or less.

17. The absorbent article of claim 16 wherein the topsheet further comprises a first edge and a second edge, the first and second edges folded over the upstanding ends and joined to the bottomsheet along the first and second sides.

18. The absorbent article of claim 16 wherein the fit factor is about 5.0 or less.

19. The absorbent article of claim 16 wherein the fit factor is about 3.0 or less.

20. The absorbent article of claim 16 wherein the length of the central portion is about 70 millimeters or greater.

21. The absorbent article of claim 16 wherein the length of the central portion is about 90 millimeters or greater.

22. The absorbent article of claim 16 wherein the central portion includes a pair of side edges and the side edges are linear.

* * * * *